United States Patent
Stack et al.

(10) Patent No.: US 9,719,838 B2
(45) Date of Patent: Aug. 1, 2017

(54) METHOD FOR CALIBRATING A MULTIPLE FLOW CONDUIT FLOW METER

(71) Applicant: Micro Motion, Inc., Boulder, CO (US)

(72) Inventors: Charles Paul Stack, Las Vegas, CO (US); Andrew Timothy Patten, Boulder, CO (US); Gregory Treat Lanham, Longmont, CO (US); Mark James Bell, Longmont, CO (US)

(73) Assignee: Micro Motion, Inc., Boulder, CO (US)

( * ) Notice: Subject to any disclaimer, the term of this patent is extended or adjusted under 35 U.S.C. 154(b) by 400 days.

(21) Appl. No.: 14/547,746

(22) Filed: Nov. 19, 2014

(65) Prior Publication Data

US 2015/0068271 A1 Mar. 12, 2015

Related U.S. Application Data

(62) Division of application No. 12/376,801, filed as application No. PCT/US2006/033024 on Aug. 24, 2006, now Pat. No. 8,919,181.

(51) Int. Cl.
*G01F 25/00* (2006.01)
*G01F 1/84* (2006.01)
*G01F 15/02* (2006.01)

(52) U.S. Cl.
CPC .......... *G01F 25/003* (2013.01); *G01F 1/8413* (2013.01); *G01F 1/8436* (2013.01); *G01F 1/8477* (2013.01); *G01F 1/8495* (2013.01); *G01F 15/024* (2013.01)

(58) Field of Classification Search
None
See application file for complete search history.

(56) References Cited

U.S. PATENT DOCUMENTS

| | | |
|---|---|---|
| 4,559,833 A | 12/1985 | Sipin |
| 4,938,075 A | 7/1990 | Lew |
| 5,072,416 A | 12/1991 | Francisco et al. |
| 5,661,232 A | 8/1997 | Van Cleve et al. |
| 6,230,104 B1 * | 5/2001 | Shelley ................. G01F 1/8413 702/45 |
| 7,845,242 B2 * | 12/2010 | McAnally ............. G01F 1/8413 73/861.355 |

(Continued)

FOREIGN PATENT DOCUMENTS

| | | |
|---|---|---|
| JP | 6227621 | 2/1987 |
| JP | 09196730 | 7/1997 |

(Continued)

*Primary Examiner* — Paul West
*Assistant Examiner* — Mark A Shabman
(74) *Attorney, Agent, or Firm* — The Ollila Law Group LLC

(57) ABSTRACT

A method for calibrating a multiple flow conduit flow meter (200) is provided according to an embodiment of the invention. The multiple flow conduit flow meter (200) includes a first flow conduit (201) conducting a first flow stream and a pair of first pickoff sensors (215, 215') affixed to the first flow conduit (201). The multiple flow conduit flow meter (200) further includes at least one additional flow conduit (202) conducting at least one additional flow stream and at least one pair of additional pickoff sensors (216, 216') affixed to the at least one additional flow conduit (202).

3 Claims, 12 Drawing Sheets

(56) References Cited

U.S. PATENT DOCUMENTS

| | | | |
|---|---|---|---|
| 8,919,181 B2 * | 12/2014 | Stack | G01F 1/8413 73/1.16 |
| 2002/0183951 A1 | 12/2002 | Cunningham et al. | |
| 2004/0200259 A1 | 10/2004 | Mattar | |

FOREIGN PATENT DOCUMENTS

| | | |
|---|---|---|
| JP | 2000505557 A | 5/2000 |
| RU | 2255968 C1 | 10/2005 |
| WO | 9733150 A2 | 9/1997 |
| WO | 0058696 A | 10/2000 |
| WO | 03046489 A1 | 5/2003 |
| WO | 2006041427 A | 4/2006 |

* cited by examiner

METHOD FOR CALIBRATING A MULTIPLE FLOW CONDUIT FLOW METER

CROSS-REFERENCE TO RELATED APPLICATION

This application claims priority from U.S. patent application Ser. No. 12/376,801, filed Feb. 9, 2009, entitled "Multiple Flow Conduit Flow Meter," and PCT/US06/33024, filed Aug. 24, 2006, entitled "Multiple Flow Conduit Flow Meter," the contents of which are incorporated herein by reference.

BACKGROUND OF THE INVENTION

1. Field of the Invention

The present invention relates to a flow meter, and more particularly to a multiple flow conduit flow meter.

2. Statement of the Problem

Vibrating conduit sensors, such as Coriolis mass flow meters and vibrating densitometers, typically operate by detecting motion of a vibrating conduit that contains a flowing material. Properties associated with the material in the conduit, such as mass flow, density and the like, can be determined by processing measurement signals received from motion transducers associated with the conduit. The vibration modes of the vibrating material-filled system generally are affected by the combined mass, stiffness and damping characteristics of the containing conduit and the material contained therein.

A typical Coriolis mass flow meter includes one or more conduits that are connected inline in a pipeline or other transport system and convey material, e.g., fluids, slurries and the like, in the system. Each conduit may be viewed as having a set of natural vibration modes including, for example, simple bending, torsional, radial, and coupled modes. In a typical Coriolis mass flow measurement application, a conduit is excited in one or more vibration modes as a material flows through the conduit, and motion of the conduit is measured at points spaced along the conduit. Excitation is typically provided by an actuator, e.g., an electromechanical device, such as a voice coil-type driver, that perturbs the conduit in a periodic fashion. Mass flow rate may be determined by measuring time delay or phase differences between motions at the transducer locations. Two such transducers (or pickoff sensors) are typically employed in order to measure a vibrational response of the flow conduit or conduits, and are typically located at positions upstream and downstream of the actuator. The two pickoff sensors are connected to electronic instrumentation by cabling, such as by two independent pairs of wires. The instrumentation receives signals from the two pickoff sensors and processes the signals in order to derive a mass flow rate measurement.

Flow meters are used to perform mass flow rate measurements for a wide variety of fluid flows. One area in which Coriolis flow meters can potentially be used is in the metering and dispensing of fuels, including alternative fuels. The alternative fuels market continues to expand in response to increasing concerns over pollution and further in response to increasing concerns about the cost and availability of unleaded gasoline and other traditional fuels. In fact, many governments are becoming involved by enacting legislation promoting the use of alternative fuels.

An opportunity for the use of Coriolis meters in the alternative fuels market is in the filling of vehicles, such as cars, buses, etc. In the prior art, the filling of individual vehicles has been performed at filling stations utilizing traditional gasoline pumps or utilizing compressed natural gas (CNG) dispensers for alternative fuels. Traditional gasoline fuel dispensers require two individual and independent meters so that two vehicles can be filled simultaneously. A dual meter fuel dispenser can provide two metered flow streams. The two flow streams can flow at different rates. The two flow streams can be of different flow materials (i.e., two different fuels, for example) and can have different densities.

However, the overall cost and size of a fuel pump for an alternative fuels must be minimized in order for the manufacture of the pump to be competitive in such a growing industry. Therefore, a challenge exists in being able to develop a cost-effective fuel meter that can provide two simultaneous fuel flow measurements on two independent flow streams.

One prior art approach is to install two separate flow meters in such a fuel dispenser. Although this is a workable approach, it has drawbacks. Two meter devices take up double the space in the fuel dispenser as a single meter device. Two meter devices can double the meter expense of a fuel dispenser. Two meter devices can require double the electrical power.

SUMMARY OF THE SOLUTION

A multiple flow conduit flow meter is provided according to an embodiment of the invention. The multiple flow conduit flow meter comprises a first flow conduit conducting a first flow stream and a pair of first pickoff sensors affixed to the first flow conduit. The multiple flow conduit flow meter further comprises at least one additional flow conduit conducting at least one additional flow stream and at least one pair of additional pickoff sensors affixed to the at least one additional flow conduit. The at least one additional flow stream is independent of the first flow stream. The multiple flow conduit flow meter further comprises a common driver configured to vibrate both the first flow conduit and the at least one additional flow conduit in order to generate a first vibrational response and at least one additional vibrational response.

A measurement method for a multiple flow conduit flow meter is provided according to an embodiment of the invention. The method comprises vibrating a first flow conduit conducting a first flow stream and vibrating at least one additional flow conduit. The vibrating is performed by a common driver. The method further comprises receiving a first vibrational response of the first flow conduit, receiving at least one additional vibrational response of the at least one additional flow conduit, and determining a first flow characteristic of the first flow stream from the first vibrational response and the at least one additional vibrational response.

A measurement method for a multiple flow conduit flow meter is provided according to an embodiment of the invention. The method comprises vibrating a first flow conduit conducting a first flow stream and vibrating at least one additional flow conduit conducting at least one additional flow stream. The vibrating is performed by a common driver. The at least one additional flow stream is independent of the first flow stream. The method further comprises receiving a first vibrational response of the first flow conduit and receiving at least one additional vibrational response of the at least one additional flow conduit. The method further comprises determining a first flow stream characteristic from the first vibrational response and the at least one additional vibrational response and determining at least one additional flow stream characteristic from the first vibrational response and the at least one additional vibrational response.

A calibration method for a multiple flow conduit flow meter is provided according to an embodiment of the invention. The method comprises zeroing out the multiple flow conduit flow meter and zeroing out one or more reference meters in communication with the multiple flow conduit flow meter. The method further comprises measuring a first flow through a first flow conduit of the multiple flow conduit flow meter using the multiple flow conduit flow meter and using the one or more reference meters and measuring at least one additional flow through at least one additional flow conduit of the multiple flow conduit flow meter using the multiple flow conduit flow meter and using the one or more reference meters. The method further comprises determining two or more flow calibration factors (FCFs) for the multiple flow conduit flow meter using a first flow measurement and an at least one additional flow measurement.

ASPECTS OF THE INVENTION

In one aspect of the flow meter, the flow meter comprises a Coriolis flow meter.

In another aspect of the flow meter, the flow meter comprises a vibrating densitometer.

In yet another aspect of the flow meter, the first flow stream and the at least one additional flow stream originate from a common input.

In yet another aspect of the flow meter, the first flow stream originates from a first input and the at least one additional flow stream originates from a second input.

In yet another aspect of the flow meter, the flow meter further comprises meter electronics configured to vibrate the first flow conduit and vibrate the at least one additional flow conduit, with the vibrating being performed by the common driver, receive a first vibrational response of the first flow conduit, receive at least one additional vibrational response of the at least one additional flow conduit, and determine a first flow characteristic of the first flow stream from the first vibrational response and the at least one additional vibrational response.

In yet another aspect of the flow meter, the flow meter further comprises meter electronics configured to vibrate the first flow conduit and vibrate the at least one additional flow conduit, with the at least one additional flow conduit conducting at least one additional flow stream, with the vibrating being performed by the common driver and with the at least one additional flow stream being independent of the first flow stream, receive a first vibrational response of the first flow conduit, receive at least one additional vibrational response of the at least one additional flow conduit, determine a first flow characteristic of the first flow stream from the first vibrational response and the at least one additional vibrational response, and determine a second flow characteristic of the at least one additional flow stream from the first vibrational response and the at least one additional vibrational response.

In yet another aspect of the flow meter, the flow meter further comprises meter electronics configured to determine a first flow characteristic and at least one additional flow characteristic using the first vibrational response and the at least one additional vibrational response in equations $$\dot{m}_1 = FCF_{11}(\Delta t_{11} - \Delta t z_{11}) \times (1 - Tc_1 \times Tm_1) + FCF_{12}(\Delta t_{12} - \Delta t z_{12}) \times (1 - Tc_2 \times Tm_2)$$

and $$\dot{m}_2 = FCF_{22}(\Delta t_{22} - \Delta t z_{22}) \times (1 - Tc_2 \times Tm_2) + FCF_{21}(\Delta t_{21} - \Delta t z_{21}) \times (1 - Tc_1 \times Tm_1)$$

in order to determine a first mass flow rate ($\dot{m}_1$) of the first flow stream and a second mass flow rate ($\dot{m}_2$) of the second flow stream.

In yet another aspect of the flow meter, the flow meter further comprises meter electronics configured to determine a first flow characteristic and at least one additional flow characteristic using the first vibrational response and the at least one additional vibrational response in equations $$\dot{m}_1 = FCF_{11}(\Delta t_1 - \Delta t z_1) \times (1 - Tc_1 \times Tm_1) + FCF_{12}(\Delta t_2 - \Delta t z_2) \times (1 - Tc_2 \times Tm_2)$$

and $$\dot{m}_2 = FCF_{22}(\Delta t_2 - \Delta t z_2) \times (1 - Tc_2 \times Tm_2) + FCF_{21}(\Delta t_1 - \Delta t z_1) \times (1 - Tc_1 \times Tm_1)$$

in order to determine a first mass flow rate ($\dot{m}_1$) of the first flow stream and a second mass flow rate ($\dot{m}_2$) of the second flow stream.

In yet another aspect of the flow meter, the flow meter further comprises meter electronics configured to zero out the multiple flow conduit flow meter for a calibration process, zero out one or more reference meters in communication with the multiple flow conduit flow meter, measure a first flow through a first flow conduit of the multiple flow conduit flow meter using the multiple flow conduit flow meter and using the one or more reference meters, measure at least one additional flow through at least one additional flow conduit of the multiple flow conduit flow meter using the multiple flow conduit flow meter and using the one or more reference meters, and determine two or more flow calibration factors (FCFs) for the multiple flow conduit flow meter using a first flow measurement and an at least one additional flow measurement.

In yet another aspect of the flow meter, the flow meter further comprises meter electronics configured to determine the two or more flow calibration factors (FCFs) for the multiple flow conduit flow meter using the equation $$\begin{Bmatrix} FCF_{11} \\ FCF_{12} \\ FCF_{21} \\ FCF_{22} \end{Bmatrix} = \begin{bmatrix} \Delta t_1^1 - z_1 & \Delta t_2^1 - z_2 & 0 & 0 \\ 0 & 0 & \Delta t_1^1 - z_1 & \Delta t_2^1 - z_2 \\ \Delta t_1^2 - z_1 & \Delta t_2^2 - z_2 & 0 & 0 \\ 0 & 0 & \Delta t_1^2 - z_1 & \Delta t_2^2 - z_2 \end{bmatrix}^{(-1)} \begin{Bmatrix} REF_1 \\ 0 \\ 0 \\ REF_2 \end{Bmatrix}.$$

In yet another aspect of the flow meter, the flow meter further comprises meter electronics configured to determine the two or more flow calibration factors (FCFs) for the multiple flow conduit flow meter using the equation $$\begin{Bmatrix} \dot{m}_1 \\ \vdots \\ \dot{m}_N \end{Bmatrix} \begin{bmatrix} FCF_{11} & \cdots & FCF_{1N} \\ \vdots & \ddots & \vdots \\ FCF_{N1} & \cdots & FCF_{NN} \end{bmatrix} \begin{Bmatrix} \Delta t_1 - z_1 \\ \vdots \\ \Delta t_N - z_N \end{Bmatrix}.$$

In one aspect of the method, the at least one additional flow conduit has zero flow.

In another aspect of the method, the at least one additional flow conduit is conducting at least one additional flow stream.

In yet another aspect of the method, the first flow stream and the at least one additional flow stream originate from a common input.

In yet another aspect of the method, the first flow stream originates from a first input and the at least one additional flow stream originates from a second input. In yet another aspect of the method, the at least one additional flow conduit conducts at least one additional flow stream that is independent of the first flow stream and the method further comprises determining at least one additional flow characteristic of the at least one additional flow stream from the first vibrational response and the at least one additional vibrational response.

In yet another aspect of the method, the determining further comprises using the first vibrational response and the at least one additional vibrational response in equations $$\dot{m}_1 = FCF_{11}(\Delta t_{11} - \Delta t z_{11}) \times (1 - Tc_1 \times Tm_1) + FCF_{12}(\Delta t_{12} - \Delta t z_{12}) \times (1 - Tc_2 \times Tm_2)$$

and $$\dot{m}_2 = FCF_{22}(\Delta t_{22} - \Delta t z_{22}) \times (1 - Tc_2 \times Tm_2) + FCF_{21}(\Delta t_{21} - \Delta t z_{21}) \times (1 - Tc_1 \times Tm_1)$$

in order to determine a first mass flow rate ($\dot{m}_1$) of the first flow stream and a second mass flow rate ($\dot{m}_2$) of the second flow stream.

In yet another aspect of the method, the determining further comprises using the first vibrational response and the at least one additional vibrational response in equations $$\dot{m}_1 = FCF_{11}(\Delta t_1 - \Delta t z_1) \times (1 - Tc_1 \times Tm_1) + FCF_{12}(\Delta t_2 - \Delta t z_2) \times (1 - Tc_2 \times Tm_2)$$

and $$\dot{m}_2 = FCF_{22}(\Delta t_2 - \Delta t z_2) \times (1 - Tc_2 \times Tm_2) + FCF_{21}(\Delta t_1 - \Delta t z_z) \times (1 - Tc_1 \times Tm_1)$$

in order to determine a first mass flow rate ($\dot{m}_1$) of the first flow stream and a second mass flow rate ($\dot{m}_2$) of the second flow stream.

In yet another aspect of the method, the method further comprises zeroing out the multiple flow conduit flow meter for a calibration process, zeroing out one or more reference meters in communication with the multiple flow conduit flow meter, measuring a first flow through the first flow conduit of the multiple flow conduit flow meter using the multiple flow conduit flow meter and using the one or more reference meters, measuring at least one additional flow through the at least one additional flow conduit of the multiple flow conduit flow meter using the multiple flow conduit flow meter and using the one or more reference meters, and determining two or more flow calibration factors (FCFs) for the multiple flow conduit flow meter using a first flow measurement and an at least one additional flow measurement.

In yet another aspect of the method, the determining comprises determining the two or more flow calibration factors (FCFs) for the multiple flow conduit flow meter using the equation $$\begin{Bmatrix} FCF_{11} \\ FCF_{12} \\ FCF_{21} \\ FCF_{22} \end{Bmatrix} = \begin{bmatrix} \Delta t_1^1 - z_1 & \Delta t_2^1 - z_2 & 0 & 0 \\ 0 & 0 & \Delta t_1^1 - z_1 & \Delta t_2^1 - z_2 \\ \Delta t_1^2 - z_1 & \Delta t_2^2 - z_2 & 0 & 0 \\ 0 & 0 & \Delta t_1^2 - z_1 & \Delta t_2^2 - z_2 \end{bmatrix}^{(-1)} \begin{Bmatrix} REF_1 \\ 0 \\ 0 \\ REF_2 \end{Bmatrix}.$$

In yet another aspect of the method, the determining comprises determining the two or more flow calibration factors (FCFs) for the multiple flow conduit flow meter using the equation $$\begin{Bmatrix} \dot{m}_1 \\ \vdots \\ \dot{m}_N \end{Bmatrix} \begin{bmatrix} FCF_{11} & \cdots & FCF_{1N} \\ \vdots & \ddots & \vdots \\ FCF_{N1} & \cdots & FCF_{NN} \end{bmatrix} \begin{Bmatrix} \Delta t_1 - z_1 \\ \vdots \\ \Delta t_N - z_N \end{Bmatrix}.$$

In one aspect of the method, the first flow stream and the at least one additional flow stream originate from a common input.

In another aspect of the method, the first flow stream originates from a first input and the at least one additional flow stream originates from a second input.

In yet another aspect of the method, the determining further comprises using the first vibrational response and the at least one additional vibrational response in equations $$\dot{m}_1 = FCF_{11}(\Delta t_{11} - \Delta t z_{11}) \times (1 - Tc_1 \times Tm_1) + FCF_{12}(\Delta t_{12} - \Delta t z_{12}) \times (1 - Tc_2 \times Tm_2)$$

and $$\dot{m}_2 = FCF_{22}(\Delta t_{22} - \Delta t z_{22}) \times (1 - Tc_2 \times Tm_2) + FCF_{21}(\Delta t_{21} - \Delta t z_{21}) \times (1 - Tc_1 \times Tm_1)$$

in order to determine a first mass flow rate ($\dot{m}_1$) of the first flow stream and a second mass flow rate ($\dot{m}_2$) of the second flow stream.

In yet another aspect of the method, the determining further comprises using the first vibrational response and the at least one additional vibrational response in equations $$\dot{m}_1 = FCF_{11}(\Delta t_1 - \Delta t z_1) \times (1 - Tc_1 \times Tm_1) + FCF_{12}(\Delta t_2 - \Delta t z_2) \times (1 - Tc_2 \times Tm_2)$$

and $$\dot{m}_2 = FCF_{22}(\Delta t_2 - \Delta t z_2) \times (1 - Tc_2 \times Tm_2) + FCF_{21}(\Delta t_1 - \Delta t z_2) \times (1 - Tc_1 \times Tm_1)$$

in order to determine a first mass flow rate ($\dot{m}_1$) of the first flow stream and a second mass flow rate ($\dot{m}_2$) of the second flow stream.

In yet another aspect of the method, the method further comprises zeroing out the multiple flow conduit flow meter for a calibration process, zeroing out one or more reference meters in communication with the multiple flow conduit flow meter, measuring a first flow through the first flow conduit of the multiple flow conduit flow meter using the multiple flow conduit flow meter and using the one or more reference meters, measuring at least one additional flow through the at least one additional flow conduit of the multiple flow conduit flow meter using the multiple flow conduit flow meter and using the one or more reference meters, and determining two or more flow calibration factors (FCFs) for the multiple flow conduit flow meter using a first flow measurement and an at least one additional flow measurement.

In yet another aspect of the method, determining comprises determining the two or more flow calibration factors (FCFs) for the multiple flow conduit flow meter using the equation $$\begin{Bmatrix} FCF_{11} \\ FCF_{12} \\ FCF_{21} \\ FCF_{22} \end{Bmatrix} = \begin{bmatrix} \Delta t_1^1 - z_1 & \Delta t_2^1 - z_2 & 0 & 0 \\ 0 & 0 & \Delta t_1^1 - z_1 & \Delta t_2^1 - z_2 \\ \Delta t_1^2 - z_1 & \Delta t_2^2 - z_2 & 0 & 0 \\ 0 & 0 & \Delta t_1^2 - z_1 & \Delta t_2^2 - z_2 \end{bmatrix}^{(-1)} \begin{Bmatrix} REF_1 \\ 0 \\ 0 \\ REF_2 \end{Bmatrix}.$$

In yet another aspect of the method, determining the two or more FCFs comprises determining the two or more FCFs using the equation $$\begin{Bmatrix} \dot{m}_1 \\ \vdots \\ \dot{m}_N \end{Bmatrix} \begin{bmatrix} FCF_{11} & \cdots & FCF_{1N} \\ \vdots & \ddots & \vdots \\ FCF_{N1} & \cdots & FCF_{NN} \end{bmatrix} \begin{Bmatrix} \Delta t_1 - z_1 \\ \vdots \\ \Delta t_N - z_N \end{Bmatrix}.$$

In one aspect of the calibration method, the determining comprises determining the two or more flow calibration factors (FCFs) for the multiple flow conduit flow meter using the equation $$\begin{Bmatrix} FCF_{11} \\ FCF_{12} \\ FCF_{21} \\ FCF_{22} \end{Bmatrix} = \begin{bmatrix} \Delta t_1^1 - z_1 & \Delta t_2^1 - z_2 & 0 & 0 \\ 0 & 0 & \Delta t_1^1 - z_1 & \Delta t_2^1 - z_2 \\ \Delta t_1^2 - z_1 & \Delta t_2^2 - z_2 & 0 & 0 \\ 0 & 0 & \Delta t_1^2 - z_1 & \Delta t_2^2 - z_2 \end{bmatrix}^{(-1)} \begin{Bmatrix} REF_1 \\ 0 \\ 0 \\ REF_2 \end{Bmatrix}.$$

In one aspect of the calibration method, the determining comprises determining the two or more flow calibration factors (FCFs) for the multiple flow conduit flow meter using the equation $$\begin{Bmatrix} \dot{m}_1 \\ \vdots \\ \dot{m}_N \end{Bmatrix} \begin{bmatrix} FCF_{11} & \cdots & FCF_{1N} \\ \vdots & \ddots & \vdots \\ FCF_{N1} & \cdots & FCF_{NN} \end{bmatrix} \begin{Bmatrix} \Delta t_1 - z_1 \\ \vdots \\ \Delta t_N - z_N \end{Bmatrix}.$$

DETAILED DESCRIPTION OF THE INVENTION

FIGS. 1-12 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
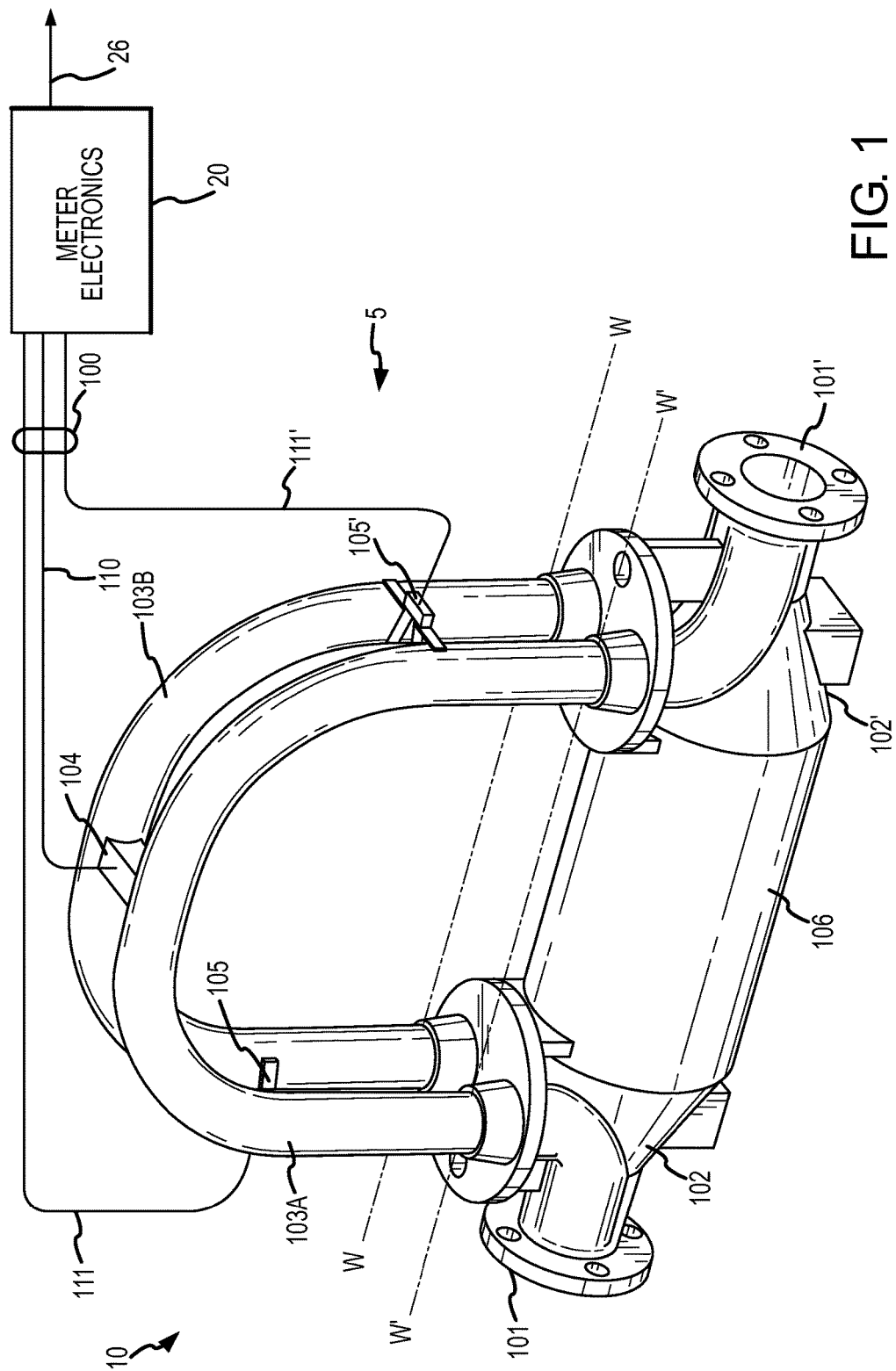
FIG. 1 illustrates a flow meter comprising a flow meter assembly and meter electronics.

FIG. 1 illustrates a flow meter 5 comprising a flow meter assembly 10 and meter electronics 20. Meter electronics 20 is connected to meter assembly 10 via leads 100 to provide density, mass flow rate, volume flow rate, totalized mass flow, temperature, and other information over path 26. It should be apparent to those skilled in the art that the present invention can be used in any type of Coriolis flow meter regardless of the number of drivers, pick-off sensors, flow conduits, or the operating mode of vibration. In addition, it should be recognized that the flow meter 5 can alternatively comprise a vibratory densitometer.

Flow meter assembly 10 includes a pair of flanges 101 and 101', manifolds 102 and 102', driver 104, pick-off sensors 105-105', and flow conduits 103A and 103B. Driver 104 and pick-off sensors 105 and 105' are connected to flow conduits 103A and 103B.

Flanges 101 and 101' are affixed to manifolds 102 and 102'. Manifolds 102 and 102' can be affixed to opposite ends of a spacer 106. Spacer 106 maintains the spacing between manifolds 102 and 102' to prevent undesired vibrations in flow conduits 103A and 103B. When flow meter assembly 10 is inserted into a conduit system (not shown) which carries the material being measured, material enters flow meter assembly 10 through flange 101, passes through inlet manifold 102 where the total amount of material is directed to enter flow conduits 103A and 103B, flows through flow conduits 103A and 103B and back into outlet manifold 102' where it exits meter assembly 10 through flange 101'.

Flow conduits 103A and 103B are selected and appropriately mounted to inlet manifold 102 and outlet manifold 102' so as to have substantially the same mass distribution, moments of inertia, and elastic modules about bending axes W—W and W'—W' respectively. The flow conduits extend outwardly from the manifolds in an essentially parallel fashion.

Flow conduits 103A and 103B are driven by driver 104 in opposite directions about their respective bending axes W and W' and at what is termed the first out of phase bending mode of the flow meter. Driver 104 may comprise one of many well known arrangements, such as a magnet mounted to flow conduit 103A and an opposing coil mounted to flow conduit 103B. An alternating current is passed through the opposing coil to cause both conduits to oscillate. A suitable drive signal is applied by meter electronics 20, via lead 110 to driver 104.

Meter electronics 20 receives sensor signals on leads 111 and 111', respectively. Meter electronics 20 produces a drive signal on lead 110 which causes driver 104 to oscillate flow conduits 103A and 103B. Meter electronics 20 processes left and right velocity signals from pick-off sensors 105 and 105' in order to compute a mass flow rate. Path 26 provides an input and an output means that allows meter electronics 20 to interface with an operator or with other electronic systems. The description of FIG. 1 is provided merely as an example of the operation of a Coriolis flow meter and is not intended to limit the teaching of the present invention.

Figure 2:
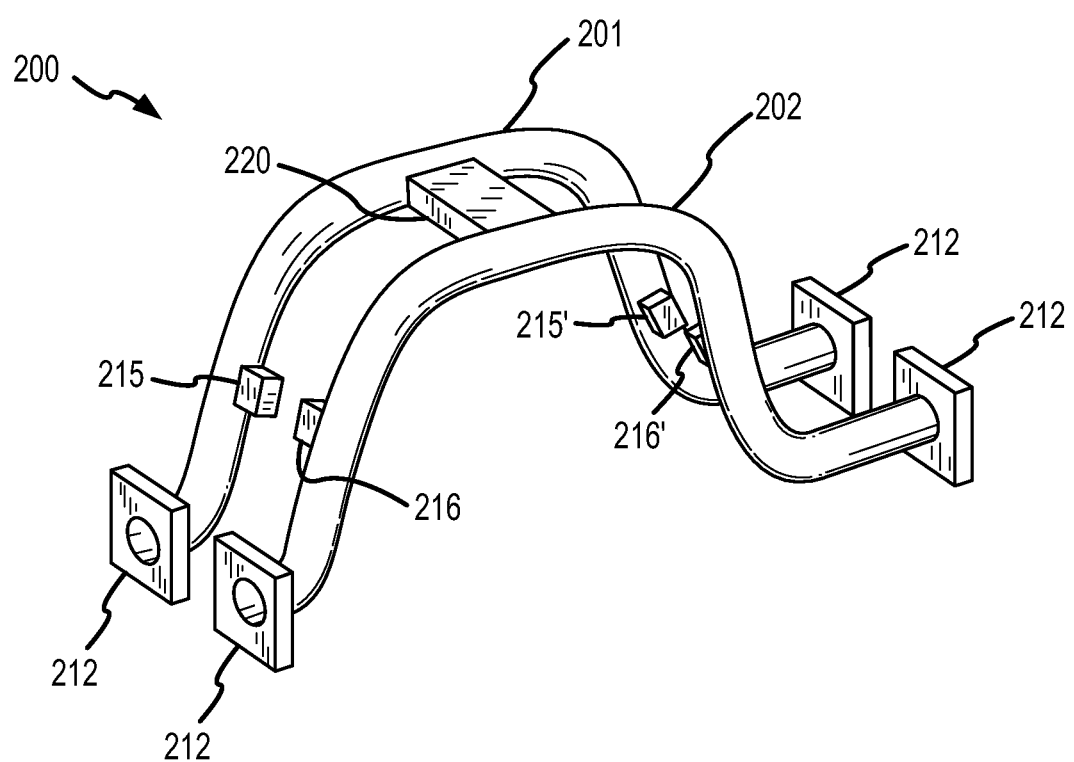
FIG. 2 is a diagram of a multiple flow conduit flow meter according to an embodiment of the invention.

FIG. 2 is a diagram of a multiple flow conduit flow meter 200 according to an embodiment of the invention. The flow meter 200 includes a first flow conduit 201 and at least one additional flow conduit 202. The two flow conduits 201 and 202 include flanges 212 at the intake and output ends. It should be understood that the multiple flow conduit flow meter 200 can include more than two flow conduits. However, only two are shown and discussed for purposes of clarity. The flow meter 200 can conduct a flow material, including a first flow stream and at least one additional flow stream that is independent of the first flow stream.

A common driver 220 is located between the first flow conduit 201 and the second flow conduit 202, wherein both flow conduits 201 and 202 are vibrated by the common driver 220. Where the multiple flow conduit flow meter 200 includes more than two flow conduits, the number of drivers will be one less than the number of flow conduits, due to the use of a driver to vibrate at least two flow conduits.

The first flow conduit 201 includes a pair of first pickoff sensors 215 and 215' positioned to detect vibration of the first flow conduit 201. The first pickoff sensors 215 and 215' can be supported by any manner of rigid support structure (not shown), wherein the pickoff sensor is held in a fixed position by the support structure and measures relative motion of the vibration of the corresponding flow conduit. The second flow conduit 202 includes a pair of second pickoff sensors 216 and 216' positioned to detect vibration of the second flow conduit 202 and also affixed to a support structure (not shown). The support structure for the pickoff sensors 215 and 215' can be the same or different than the support structure employed for the pickoff sensors 216 and 216'. Upon vibration of the flow conduits 201 and 202, the pair of first pickoff sensors 215 and 215' generate a flow characteristic measurement for the first flow conduit 201 and the pair of second pickoff sensors 216 and 216' generate a flow characteristic measurement for the second flow conduit 202.

The flow characteristic measurements from the pair of first pickoff sensors 215 and 215' and from the pair of second pickoff sensors 216 and 216' are received and processed by the meter electronics 20 (see FIG. 1). The meter electronics 20 can generate a first flow measurement related to the first flow stream and can generate a second flow measurement related to the second flow stream. The processing can generate mass flow rate and/or density measurements, for example.

Another flow characteristic that can be generated by the processing is a viscosity value for each flow stream. If the two flow conduits are of different flow areas, for example the multiple flow conduit flow meter 200 can be configured to measure dynamic viscosity and coating. Other flow characteristics can also be generated by the processing and are within the scope of the description and claims.

The first flow stream is independent of the second flow stream. As a result, the first flow stream is not linked to or influenced by the second flow stream, and vice versa. Consequently, the flow through each flow conduit can be measured and controlled independently of the flow through the other conduit.

In one embodiment, the first flow stream can have a different flow rate than the second flow stream. In one embodiment, the first flow stream can comprise a first flow material and the second flow stream can comprise a second flow material. The first flow stream can have a first density and the second flow stream can have a second density. For example, the first flow stream can comprise a first fuel and the second flow stream can comprise a second fuel. The fuels can be flowing at different rates. Therefore, the first and second flow measurements can be used by the meter electronics 20 to conduct two independent fuel metering transactions, for example.

In one embodiment, the flow conduits 201 and 202 comprise substantially U-shaped flow conduits, as shown. Alternatively, in an embodiment shown in FIG. 5 and discussed below, the flow conduits 201 and 202 can comprise substantially straight flow conduits. However, other shapes can also be used, and are within the scope of the description and claims.

In one embodiment, the first flow conduit 201 has the same cross-sectional area as the second flow conduit 202. Alternatively, they can have differing cross-sectional areas.

Figure 3:
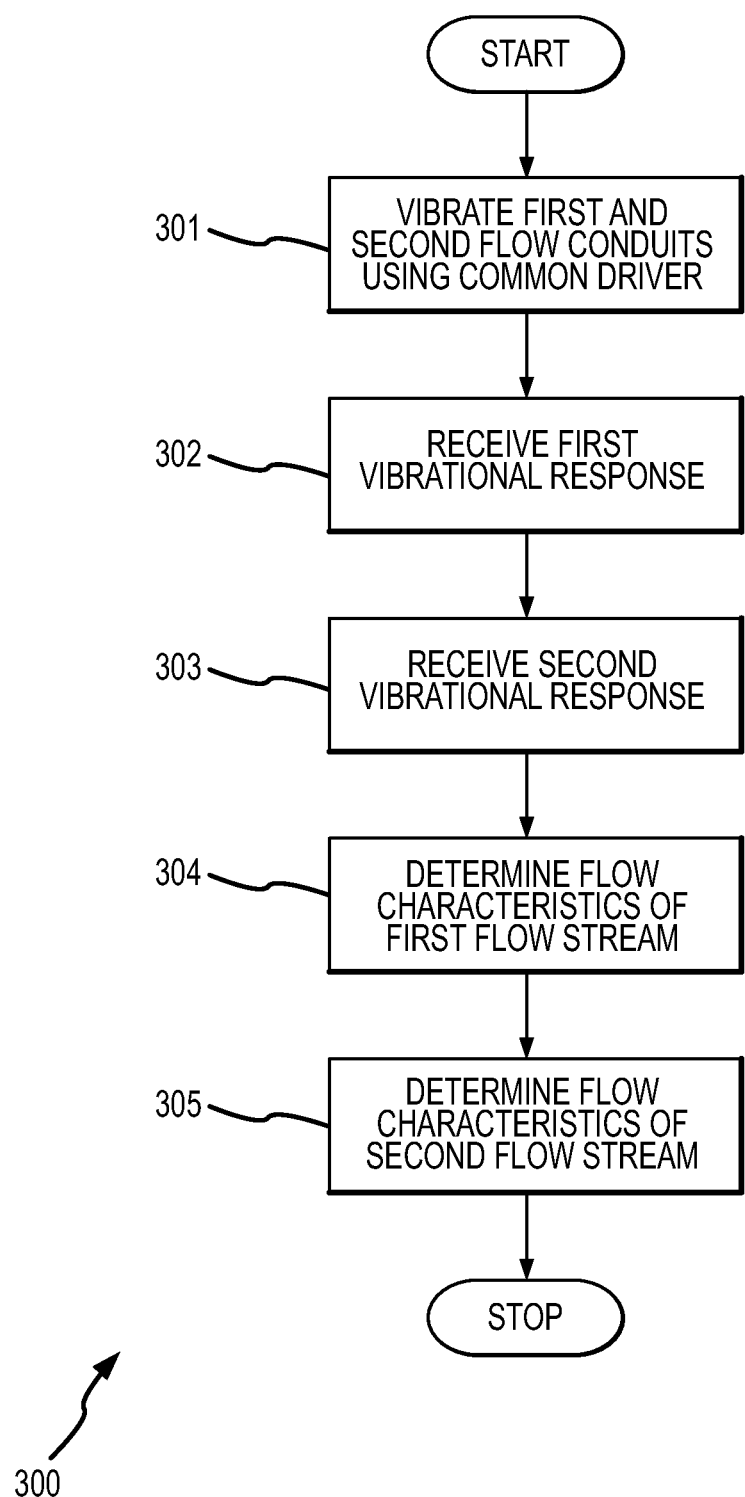
FIG. 3 is a flowchart of a measurement method for a multiple flow conduit flow meter according to an embodiment of the invention.

FIG. 3 is a flowchart 300 of a measurement method for a multiple flow conduit flow meter according to an embodiment of the invention. The method can be used to measure flow through just the first flow conduit, to measure flow through just the second flow conduit, or to measure flow simultaneously through both the first and second flow conduits.

In step 301, the first flow conduit and the second flow conduit are vibrated by a common driver 220. The first flow conduit can conduct a first flow stream and the second flow conduit can conduct a second flow stream. The flow conduits in one embodiment each have separate sets of pickoff sensors (see FIG. 2). Alternatively, in another embodiment the flow conduits share a set of pickoff sensors (see FIG. 4).

In step 302, a first vibrational response of the first flow conduit is received. The first vibrational response can comprise an electrical signal generated by a set of pickoff sensors, wherein the electrical signal is related to the first vibrational response. The first flow material is flowing in the first flow conduit. The first vibrational response therefore can include a vibrational response of a flow material in the first flow conduit.

In step 303, a second vibrational response of the second flow conduit is received. The second vibrational response can comprise an electrical signal generated by a set of pickoff sensors, wherein the electrical signal is related to the second vibrational response. The second vibrational response therefore can include a vibrational response of a flow material in the second flow conduit, can include a non-flow vibrational response, or can include a vibrational response of the empty second flow conduit.

In step 304, a first flow characteristic of the first flow stream is determined. It should be understood that more than one first flow characteristic can be determined in this step. The first flow characteristic is determined from the first and the at least one additional vibrational responses. The first flow characteristic can comprise a mass flow rate ($\dot{m}_1$) of the first flow material. In addition, the density, viscosity, etc., of the first flow material can be determined from the first and the at least one additional vibrational responses.

In step 305, a second flow characteristic of the at least one additional flow stream is determined. It should be understood that more than one flow characteristic for the at least one additional flow stream can be determined in this step. The second flow characteristic is determined from the first and at least one additional vibrational responses. The second flow characteristic can comprise a mass flow rate ($\dot{m}_2$) of the second flow material. In addition, the density, viscosity, etc., of the second flow material can be determined from the first and the at least one additional vibrational responses.

Although the flow through each flow conduit is independent, the measurement of mass flow in one flow conduit is not independent of the flow through the other conduit. A flow through one conduit induces a phase in the other conduit. Because of this linkage, a new mass flow equation is used in the multiple flow conduit flow meter 200 according to the invention. The new dual flow conduit equations are based on the time delay experienced by both flow conduits 201 and 202 (i.e., $\Delta t_1$ and $\Delta t_2$).

In a traditional dual tube Coriolis flow meter, a phase is measured between two flow conduits and a phase difference is calculated between inlet side pickoffs and outlet side pickoffs of the meter. This phase difference is converted into a single time delay ($\Delta t$) and is used to determine a flow amount (such as a mass flow rate $\dot{m}$, for example), by employing the equation:

$$\dot{m} = FCF \times (\Delta t - \Delta tz) * (1 - T_c \times T) \quad (1)$$

In this equation, a single measurement of time delay ($\Delta t$) can be used to measure flow. The time delay ($\Delta t$) is adjusted by a time delay at zero ($\Delta tz$). The time delay at zero ($\Delta tz$) comprises a calibration factor that is determined under no-flow conditions.

However, this traditional mass flow rate equation is not adequate for a multiple flow conduit flow meter. The reason is that in the dual flow conduits of the invention, the flow induces some phase in both flow conduits. This is true even when there is flow in only one of the two flow conduits. In the traditional flow meter, because a common flow passes through both flow conduits, the induced phase is identical in each conduit. As a result, the induced phase does not appear as a phase difference between the two conduits and is not a factor in calculating a result. Therefore, a single time delay can be used in the prior art in order to determine a flow rate in a traditional flow meter.

In contrast, in the invention the first and second flow streams are independent. As a consequence, phase induced by the two flows may differ between the two flow conduits. Therefore, a mass flow rate equation based on a single time delay cannot be employed.

Flow in the multiple flow conduit flow meter 200 induces phase in both flow conduits 201 and 202, even though flow may only exist in one of the flow conduits. The two induced phases may differ. As a result, two time delay measurements are required from each flow conduit in order to measure flow. The flow measurement can be for one or two flows. One illustration of this measurement scheme can be illustrated with the following equations:

$$\dot{m}_1 = FCF_{11}(\Delta t_{11} - \Delta tz_{11}) \times (1 - Tc_1 \times Tm_1) + FCF_{12}(\Delta t_{12} - \Delta tz_{12}) \times (1 - Tc_2 \times Tm_2) \quad (2)$$

$$\dot{m}_2 = FCF_{22}(\Delta t_{22} - \Delta tz_{22}) \times (1 - Tc_2 \times Tm_2) + FCF_{21}(\Delta t_{21} - \Delta tz_{21}) \times (1 - Tc_1 \times Tm_1) \quad (3)$$

where the subscript 1 refers to the first flow tube and the subscript 2 refers to the second flow tube. The second term in equations (2) and (3) (i.e., for the "2" of the $FCF_{12}$ term, for example) is required due to the fact that flow through one flow tube induces a phase in the other tube. Equations (2) and (3) can be used in the meter electronics 20 for determining mass flow rates in both flow conduits 201 and 202.

Hereinafter, for time delay values of the form ($\Delta t_B^A$), the superscript A denotes which flow conduit is conducting flow. If flow is being conducted through the second flow conduit 202, then the time delay value will be of the form ($\Delta t_B^2$). The subscript B denotes the flow conduit that a vibrational response is being received from. Therefore, the value ($\Delta t_2^1$) is the time delay measured for the second flow conduit wherein the flow is through the first flow conduit. Alternatively, the value ($\Delta t_1^2$) is the time delay measured for the first flow conduit wherein the flow is through the second flow conduit 202. A superscript of zero denotes a no-flow condition, wherein the value ($\Delta t_1^0$) denotes a time delay measured for the first flow conduit 201 wherein the first flow conduit is vibrated by the common driver 220 under a zero or no-flow condition.

However, a simpler form of equations (2) and (3) can be used for determining the flow characteristics. Equations (2) and (3) do not take advantage of any symmetry. One possible form of symmetry is in the time delay. If the time delay is symmetric, i.e., if:

$$\Delta t_{11} \cong \Delta t_1 \quad (4a)$$

$$\Delta t_{12} \cong \Delta t_2 \quad (4b)$$

$$\Delta t_{21} \cong \Delta t_1 \quad (4c)$$

$$\Delta t_{22} \cong \Delta t_2 \quad (4d)$$

then equations (2) and (3) become:

$$\dot{m}_1 = FCF_{11}(\Delta t_1 - \Delta tz_1) \times (1 - M_1 \times Tm_1) + FCF_{12}(\Delta t_2 - \Delta tz_2) \times (1 - Tc_2 \times Tm_2) \quad (5)$$

$$\dot{m}_2 = FCF_{22}(\Delta t_2 - \Delta tz_2) \times (1 - Tc_2 \times Tm_2) + FCF_{21}(\Delta t_1 - \Delta tz_1) \times (1 - M_1 \times Tm_1) \quad (6)$$

The T terms represent temperature measurements. The $Tc_1$ term is the temperature of the first flow conduit and the $Tm_1$ term is the temperature of the first flow fluid. Likewise, the $Tc_2$ term is the temperature of the second flow conduit and the $Tm_2$ term is the temperature of the second flow fluid. The ($\Delta tz_1$) value is the zero flow calibration value for the first flow conduit and the ($\Delta tz_2$) value is the zero flow calibration value for the second flow conduit. The flow calibration factors $FCF_{11}$, $FCF_{12}$, $FCF_{21}$, and $FCF_{22}$ are calibration coefficients that are determined by flow tests and subsequently are used in flow characteristic calibrations.

Additionally, the flow calibration factors could also be symmetric. In this case, equations (5) and (6) would be further simplified by the fact that the flow calibration factors may be approximately symmetrical, i.e., $FCF_{12} \cong FCF_{21}$. The symmetry of the equations would influence the calibration process.

The ability to measure two mass flow rates may also make it possible to measure additional process variables beyond just the two mass flow rates. For instance, if the two flow conduits are of different cross-sectional flow areas, the ratio of the two flow rates can be related to dynamic viscosity. Another potential application would be the measurement of coating on the interior surfaces of the flow conduits. Such flow conduit coating will induce an unbalanced mass in the system and this unbalanced mass may be detectable through a ratio of amplitudes of the two resulting flow conduit vibrational responses. These are just two examples of what may be feasible with a flow meter that measures two independent flow streams.

The calibration procedure for a prior art single flow Coriolis meter represented by equation (1) is quite simple. The time delay at zero ($\Delta tz$) is determined under zero flow conditions in the multiple flow conduit flow meter 200 and the FCF value is determined with a test at a single flow rate.

It can be seen from equations (2) and (3) and (5) and (6) that a similar strategy (measure ($\Delta tz$) at zero and test at one flow rate per tube) would not work for a multiple flow conduit flow meter.

Figure 4:
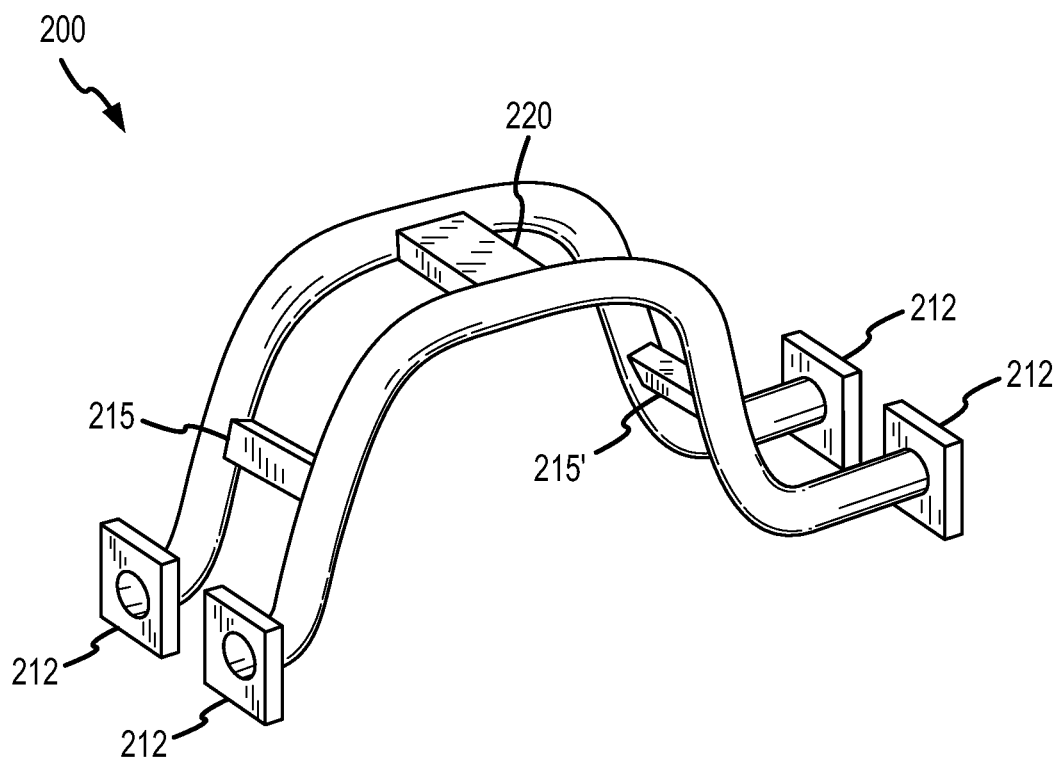
FIG. 4 shows a multiple flow conduit flow meter according to an embodiment of the invention.

FIG. 4 shows a multiple flow conduit flow meter 200 according to an embodiment of the invention. Components in common with other figures share reference numbers. In this embodiment, only one pair of pickoff sensors 215 and 215' are positioned between the first and second flow conduits 201 and 202. The pickoff sensor pair 215 and 215' measure vibrations in both flow conduits and each pickoff sensor 215 and 215' provides a signal related to the time delay between the two flow conduits.

Figure 5:
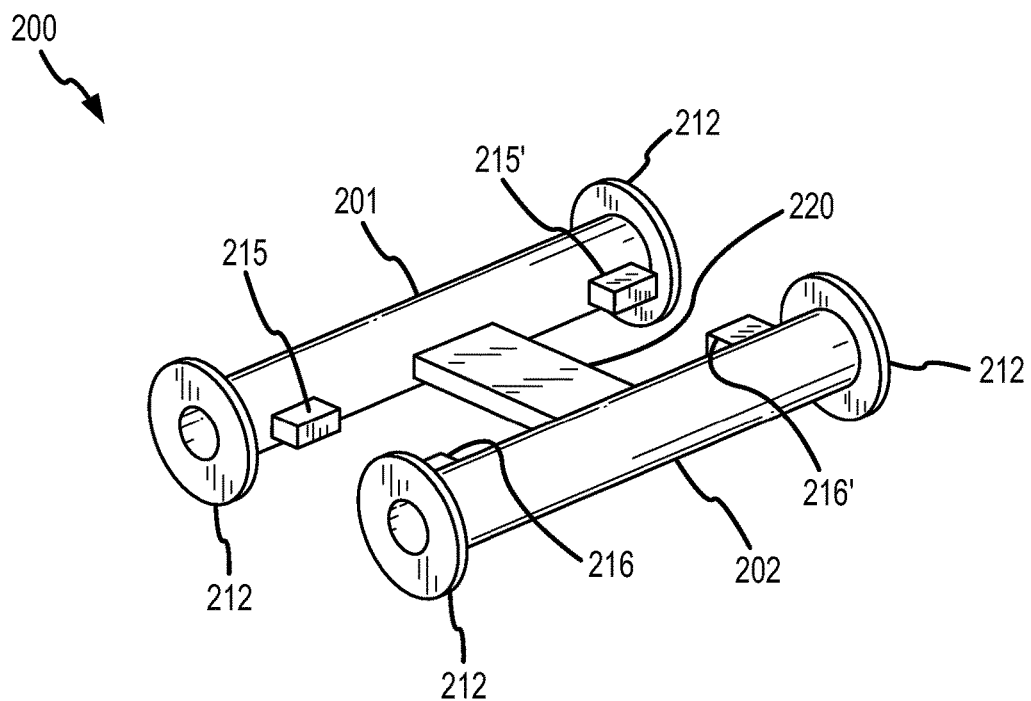
FIG. 5 shows a straight tube multiple flow conduit flow meter according to an embodiment of the invention.

FIG. 5 shows a straight tube multiple flow conduit flow meter 200 according to an embodiment of the invention. In this embodiment, the flow conduits 201 and 202 are substantially straight. It should be understood that the flow meter 200 of this embodiment can include two sets of pickoffs, as in FIG. 2, or can include one set of pickoffs, as in FIG. 4.

Figure 6:
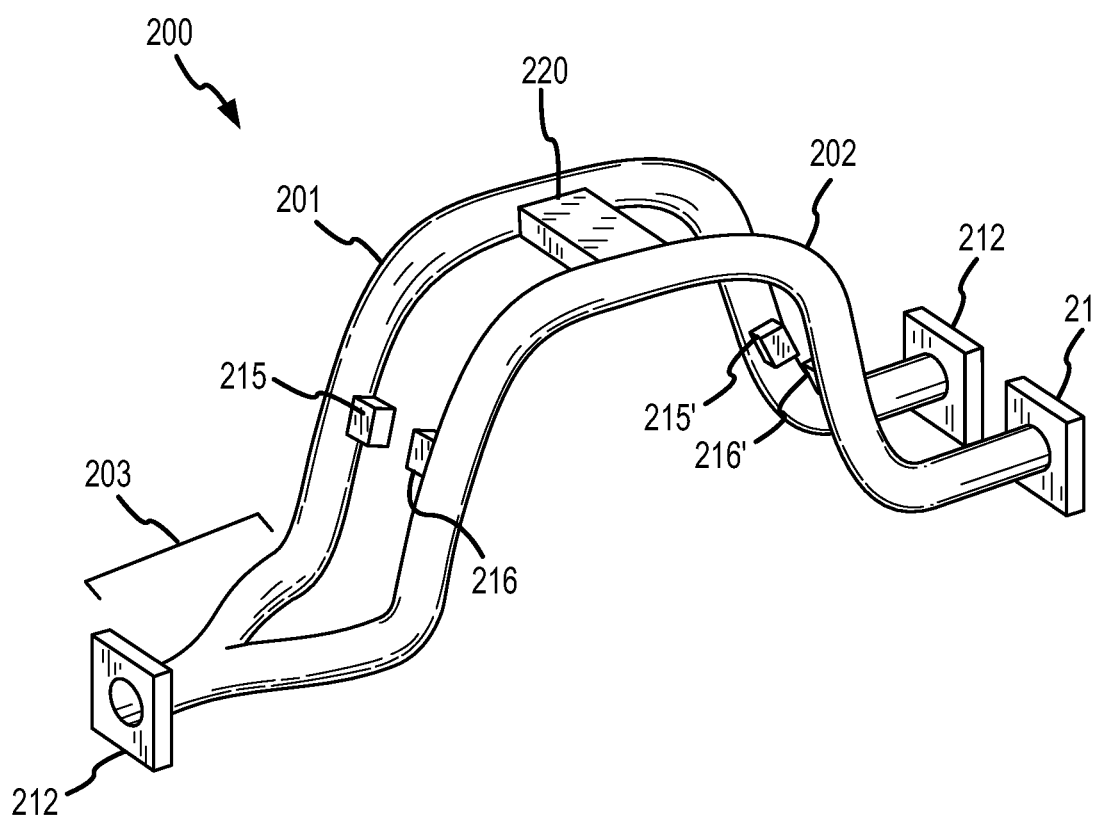
FIG. 6 shows a multiple flow conduit flow meter according to an embodiment of the invention.

FIG. 6 shows a multiple flow conduit flow meter 200 according to an embodiment of the invention. In this embodiment, the flow meter 200 includes a common inlet in the form of a flow divider 203. The flow divider 203 is coupled to both the first flow conduit 201 and to the second flow conduit 202. In this embodiment, each flow conduit has a pair of associated pickoff sensors 215 and 215' and pickoff sensors 216 and 216', as previously discussed. Downstream devices (not shown) can provide flow regulation or flow control.

Figure 7:
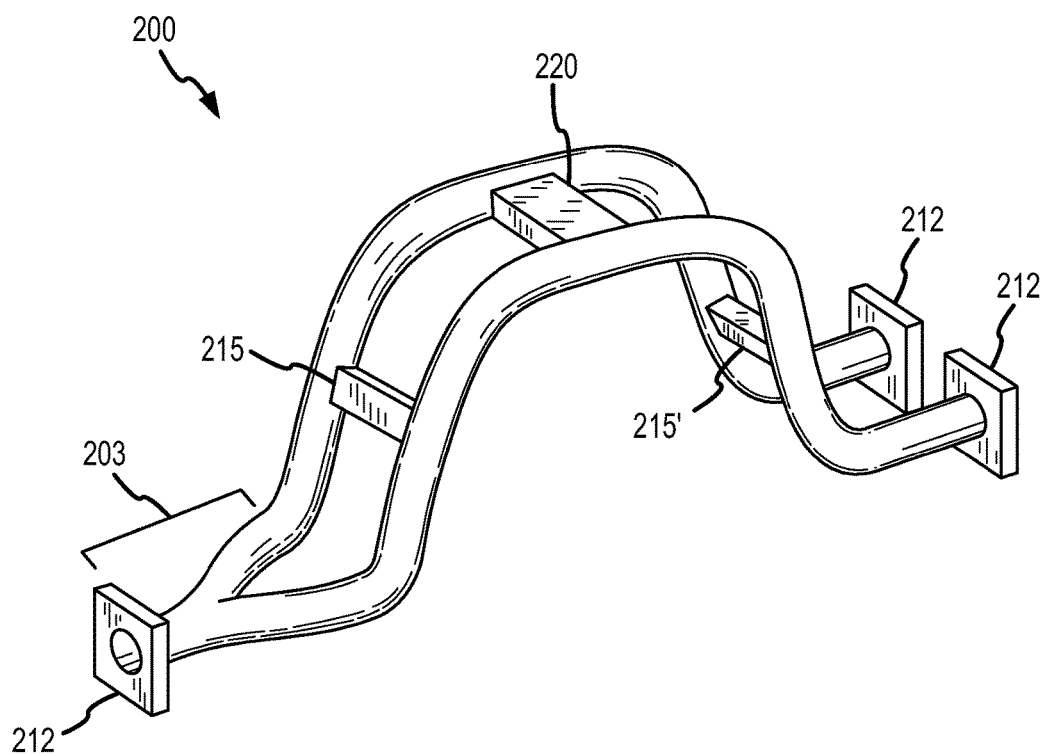
FIG. 7 shows a multiple flow conduit flow meter according to an embodiment of the invention.

FIG. 7 shows a multiple flow conduit flow meter 200 according to an embodiment of the invention. This embodiment includes the flow divider 203, as in FIG. 6. However, only one pair of pickoff sensors 215 and 215' are included in this embodiment. As in FIG. 4, the pickoff sensor pair 215 and 215' measures the simultaneous vibrations of both flow conduits 201 and 202.

Figure 8:
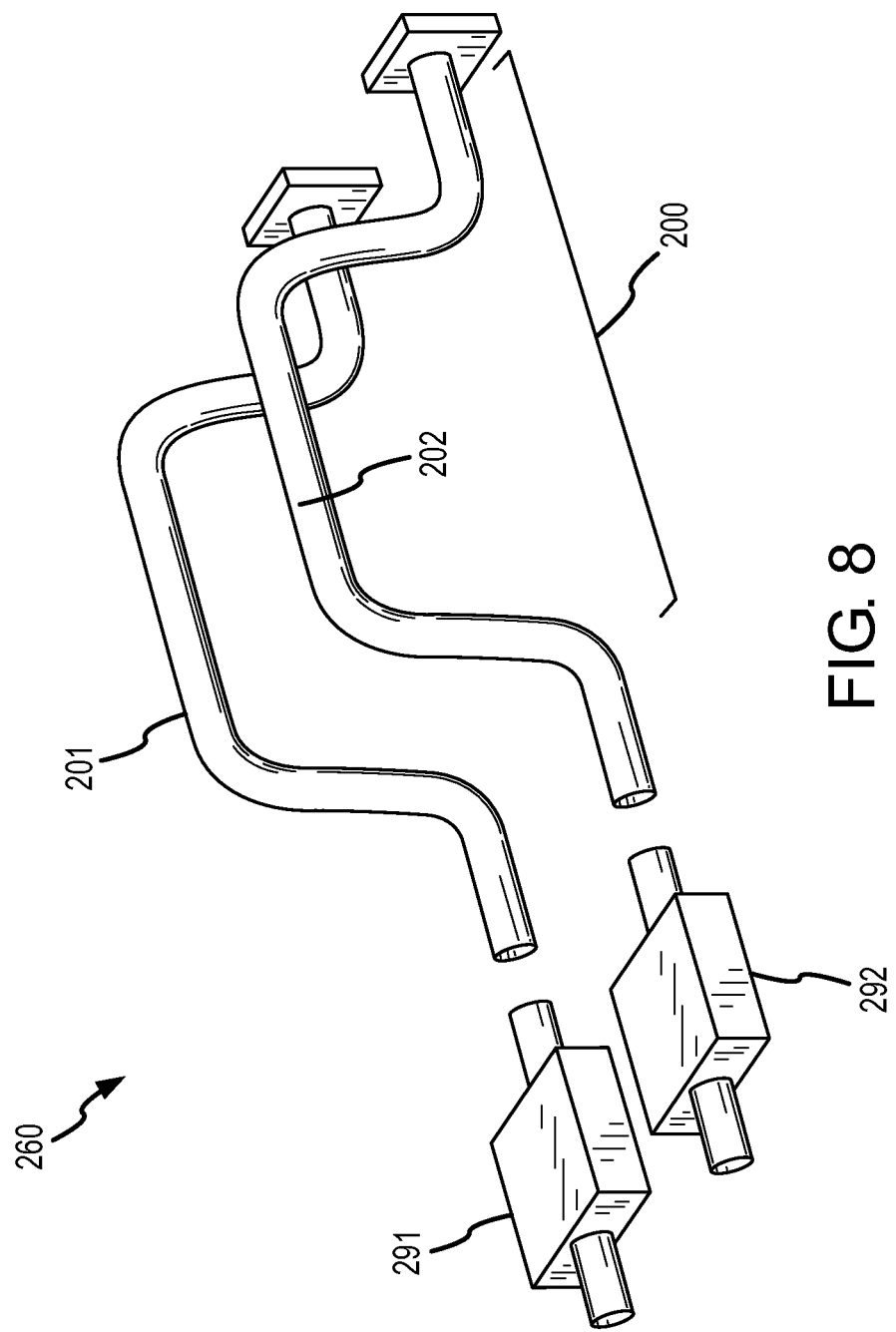
FIG. 8 shows a multiple flow conduit flow meter in a calibration set-up according to an embodiment of the invention.

FIG. 8 shows a multiple flow conduit flow meter 200 in a calibration set-up 260 according to an embodiment of the invention. In this embodiment, where the multiple flow conduit flow meter 200 has separate inlets and separate outlets, first and second reference meters 291 and 292 are employed for the calibration process. The reference meters 291 and 292 are flow meters that are used to accurately measure flow conditions, wherein the meter under test is calibrated using measurements obtained from the reference meters 291 and 292.

The first reference meter 291 measures the first flow stream flowing through the first flow conduit 201 and generates a ($\dot{m}_1$) measurement value. The second reference meter 292 measures the second flow stream flowing through the second flow conduit 202 and generates a ($\dot{m}_2$) measurement value. Therefore, the flow through each flow conduit and associated reference meter is separate from and independent of the flow through the other flow conduit. In addition, other flow measurements can be obtained.

The obtained measurements can be used for calibrating the multiple flow conduit flow meter 200 according to the various embodiments. Possible calibration operations are discussed below, such as in conjunction with FIG. 10. However, other calibration techniques are contemplated and are within the scope of the description and claims.

Figure 9:
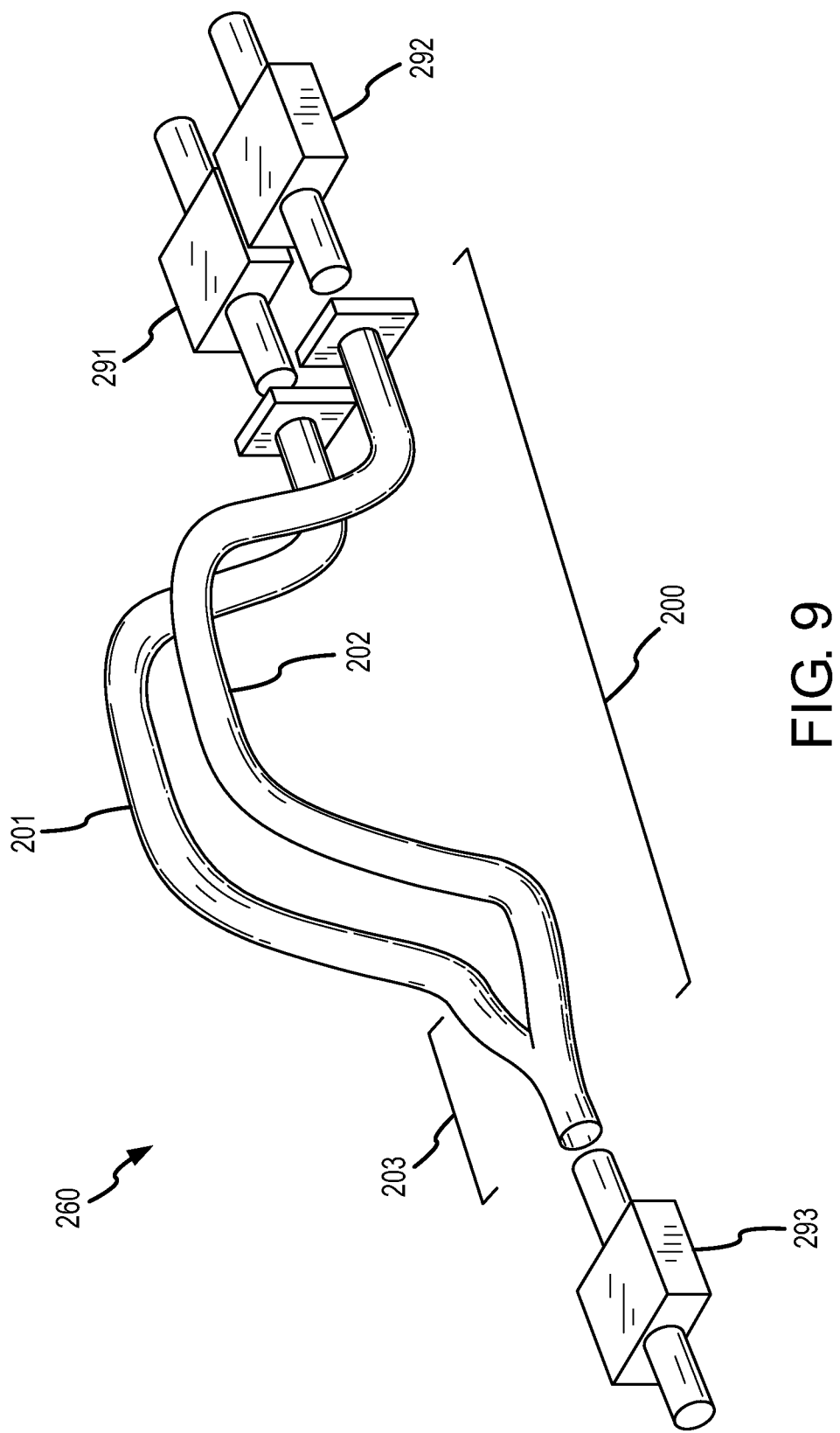
FIG. 9 shows a multiple flow conduit flow meter in a calibration set-up according to an embodiment of the invention.

FIG. 9 shows a multiple flow conduit flow meter 200 in a calibration set-up 260 according to an embodiment of the invention. In this embodiment, where the flow meter 200 has a single inlet, the first and second reference meters 291 and 292 are connected to the respective outlets of the first and second flow conduits 201 and 202. Flow through the first and second flow conduits 201 and 202 can be controlled by downstream valves or other devices (not shown) that are in communication with the two outlets. As before, the first reference meter 291 measures the first flow stream flowing through the first flow conduit 201 and generates a ($\dot{m}_1$) measurement value. The second reference meter 292 measures the second flow stream flowing through the second flow conduit 202 and generates a ($\dot{m}_2$) measurement value. In addition, the calibration set-up 260 can include a reference meter 293 that measures a total mass flow rate ($\dot{m}$) going into the multiple flow conduit flow meter 200.

Figure 10:
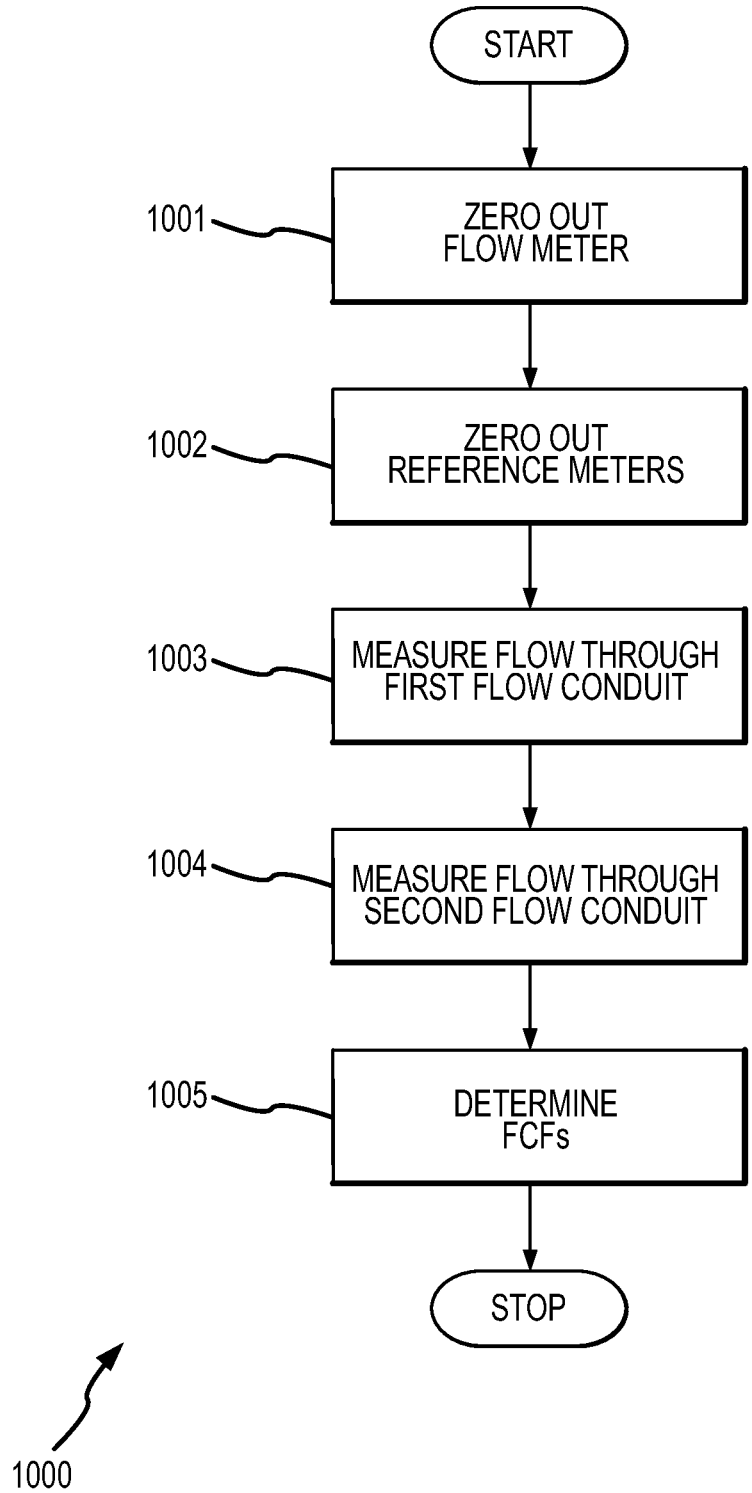
FIG. 10 is a flowchart for a multiple flow conduit flow meter calibration method according to an embodiment of the invention.

FIG. 10 is a flowchart 1000 for a multiple flow conduit flow meter calibration method according to an embodiment of the invention. A basic equation for calibration comprises:

$$\begin{Bmatrix} \dot{m}_1 \\ \dot{m}_2 \end{Bmatrix} = \begin{bmatrix} FCF_{11} & FCF_{12} \\ FCF_{21} & FCF_{22} \end{bmatrix} \begin{Bmatrix} \Delta t_1 - z_1 \\ \Delta t_2 - z_2 \end{Bmatrix} \quad (7)$$

In step 1001, the multiple flow conduit flow meter 200 (i.e., the device under test, see FIGS. 8 and 9) is zeroed out. In this step, both flow conduits 201 and 202 of the flow meter 200 are filled with flow material, although no flow is permitted through the flow meter 200. The flow conduits 201 and 202 are vibrated under the no-flow condition and one or more flow characteristics are determined, such as the $\Delta t_1^0$ and $\Delta t_2^0$ time delay values for the first and second flow conduits, for example.

For step 1001, where the flow is zero (mass flow rate $\dot{m}=0$) and a zeroing operation is being performed, equation (7) becomes:

$$\begin{Bmatrix} 0 \\ 0 \end{Bmatrix} = \begin{bmatrix} FCF_{11} & FCF_{12} \\ FCF_{21} & FCF_{22} \end{bmatrix} \begin{Bmatrix} \Delta t_1^0 - z_1 \\ \Delta t_2^0 - z_2 \end{Bmatrix} \Rightarrow \begin{Bmatrix} z_1 \\ z_2 \end{Bmatrix} = \begin{Bmatrix} \Delta t_1^0 \\ \Delta t_2^0 \end{Bmatrix} \quad (8)$$

In step 1002, the reference meters 291 and 292 are zeroed out under zero flow conditions, as described immediately above. It should be understood that this step can be performed before or after step 1001.

In step 1003, flow is generated only through the first flow conduit 201. During the flow, both the flow meter 200 and the first reference meter 291 measure first flow characteristics. For example, the flow meter 200 can record a time delay ($\Delta t_1^1$) for the first flow conduit 201 with the flow being through the first flow conduit 201. The flow meter 200 measures a time delay ($\Delta t_2^1$) for the second flow conduit 202 during the flow through the first flow conduit 201 but where there is no flow through the second flow conduit 202. In addition, the first reference meter 291 measures the mass flow rate of the flow through the first flow conduit 201 (i.e., it generates the $REF_1$ value). For step 1003, where flow is generated in the first flow conduit 201, then equation (7) becomes:

$$\left\{ \begin{array}{c} \dot{m}_1 \\ \dot{m}_2 \end{array} \right\} = \begin{bmatrix} FCF_{11} & FCF_{12} \\ FCF_{21} & FCF_{22} \end{bmatrix} \left\{ \begin{array}{c} \Delta t_1^1 - z_1 \\ \Delta t_2^1 - z_2 \end{array} \right\} = \left\{ \begin{array}{c} REF_1 \\ 0 \end{array} \right\} \quad (9)$$

In step 1004, flow is generated through the second flow conduit 202. During the flow, both the multiple flow conduit flow meter 200 and the second reference meter 292 measure second flow characteristics. For example, the flow meter 200 measures a time delay ($\Delta t_2^2$) for the second flow conduit 202 with the flow being through the second flow conduit 202. The flow meter 200 measures a time delay ($\Delta t_2^1$) for the first flow conduit 201 during the flow through the second flow conduit 202 but where there is no flow through the first flow conduit 201. In addition, the second reference meter 292 measures the mass flow rate of the flow through the second flow conduit 202 (i.e., it generates the $REF_2$ value). For step 1004, where flow is generated in the second flow conduit 202, then equation (7) becomes:

$$\left\{ \begin{array}{c} \dot{m}_1 \\ \dot{m}_2 \end{array} \right\} = \begin{bmatrix} FCF_{11} & FCF_{12} \\ FCF_{21} & FCF_{22} \end{bmatrix} \left\{ \begin{array}{c} \Delta t_1^2 - z_1 \\ \Delta t_2^2 - z_2 \end{array} \right\} = \left\{ \begin{array}{c} 0 \\ REF_2 \end{array} \right\} \quad (10)$$

It should be noted that the $REF_1$ and $REF_2$ values can be generated by two different reference meters (see FIG. 9). Alternatively, the $REF_1$ and $REF_2$ values can be generated at different times by a single reference meter (see FIG. 11).

In step 1005, the various flow characteristic measurements obtained above are inserted into a (4×4) matrix (see equation (13) below). A matrix inversion is solved in order to generate the flow calibration factors $FCF_{11}$, $FCF_{12}$, $FCF_{21}$, and $FCF_{22}$. These flow calibration factors are used for subsequent flow characteristic computations, including normal operational determinations of mass flow rate, density, viscosity, etc.

There are now 4 equations and 4 unknowns. The known (i.e., measured) quantities are $REF_1$, $REF_2$, $\Delta t_1^1$, $\Delta t_2^1$, $\Delta t_1^2$, $\Delta t_2^2$, $\Delta t_1^0$, and $\Delta t_2^0$. It should be recalled that, per the zeroing step:

$$z_1 = \Delta t_1^0 \quad (11a)$$

$$z_2 = \Delta t_2^0 \quad (11b)$$

The unknown quantities are the flow calibration factors $FCF_{11}$, $FCF_{12}$, $FCF_{21}$, and $FCF_{22}$. These FCFs are the values that are to be determined in the calibration process.

This can then be assembled into a 4×4 matrix equation:

$$\begin{bmatrix} \Delta t_1^1 - z_1 & \Delta t_2^1 - z_2 & 0 & 0 \\ 0 & 0 & \Delta t_1^1 - z_1 & \Delta t_2^1 - z_2 \\ \Delta t_1^2 - z_1 & \Delta t_2^2 - z_2 & 0 & 0 \\ 0 & 0 & \Delta t_1^2 - z_1 & \Delta t_2^2 - z_2 \end{bmatrix} \left\{ \begin{array}{c} FCF_{11} \\ FCF_{12} \\ FCF_{21} \\ FCF_{22} \end{array} \right\} = \left\{ \begin{array}{c} REF_1 \\ 0 \\ 0 \\ REF_2 \end{array} \right\} \quad (12)$$

Then solved with a 4×4 matrix inverse:

$$\left\{ \begin{array}{c} FCF_{11} \\ FCF_{12} \\ FCF_{21} \\ FCF_{22} \end{array} \right\} = \begin{bmatrix} \Delta t_1^1 - z_1 & \Delta t_2^1 - z_2 & 0 & 0 \\ 0 & 0 & \Delta t_1^1 - z_1 & \Delta t_2^1 - z_2 \\ \Delta t_1^2 - z_1 & \Delta t_2^2 - z_2 & 0 & 0 \\ 0 & 0 & \Delta t_1^2 - z_1 & \Delta t_2^2 - z_2 \end{bmatrix}^{(-1)} \left\{ \begin{array}{c} REF_1 \\ 0 \\ 0 \\ REF_2 \end{array} \right\} \quad (13)$$

In another embodiment, the multiple flow conduit flow meter 200 according to the invention can include more than two flow conduits. For example, the multiple flow conduit flow meter 200 can include N flow conduits. A starting assumption is that multiple flow conduits behave substantially identically to a meter having two flow conduits. With three flow conduits, the matrix equation becomes:

$$\left\{ \begin{array}{c} \dot{m}_1 \\ \dot{m}_2 \\ \dot{m}_3 \end{array} \right\} \begin{bmatrix} FCF_{11} & FCF_{12} & FCF_{13} \\ FCF_{21} & FCF_{22} & FCF_{23} \\ FCF_{31} & FCF_{32} & FCF_{33} \end{bmatrix} \left\{ \begin{array}{c} \Delta t_1 - z_1 \\ \Delta t_2 - z_2 \\ \Delta t_2 - z_2 \end{array} \right\} \quad (14)$$

Using the same nomenclature for this three flow conduit example, the result is nine unknowns (i.e., the FCF matrix in equation 14 above) requiring three different flow calibration points. At each calibration point of the three calibration points, the ($\Delta t$) measurements are recorded, along with the three zero reference flow rates ($z$). Calibration point 1 comprises:

$$\left\{ \begin{array}{c} REF_{11} \\ REF_{12} \\ REF_{13} \end{array} \right\} = \begin{bmatrix} FCF_{11} & FCF_{12} & FCF_{13} \\ FCF_{21} & FCF_{22} & FCF_{23} \\ FCF_{31} & FCF_{32} & FCF_{33} \end{bmatrix} \left\{ \begin{array}{c} \Delta t_1^1 - z_1 \\ \Delta t_2^1 - z_2 \\ \Delta t_3^1 - z_3 \end{array} \right\} \quad (15)$$

Calibration point 2 comprises:

$$\left\{ \begin{array}{c} REF_{21} \\ REF_{22} \\ REF_{23} \end{array} \right\} = \begin{bmatrix} FCF_{11} & FCF_{12} & FCF_{13} \\ FCF_{21} & FCF_{22} & FCF_{23} \\ FCF_{31} & FCF_{32} & FCF_{33} \end{bmatrix} \left\{ \begin{array}{c} \Delta t_1^2 - z_1 \\ \Delta t_2^2 - z_2 \\ \Delta t_3^2 - z_3 \end{array} \right\} \quad (16)$$

Calibration point 3 comprises:

$$\left\{ \begin{array}{c} REF_{31} \\ REF_{32} \\ REF_{33} \end{array} \right\} = \begin{bmatrix} FCF_{11} & FCF_{12} & FCF_{13} \\ FCF_{21} & FCF_{22} & FCF_{23} \\ FCF_{31} & FCF_{32} & FCF_{33} \end{bmatrix} \left\{ \begin{array}{c} \Delta t_1^3 - z_1 \\ \Delta t_2^3 - z_2 \\ \Delta t_3^3 - z_3 \end{array} \right\} \quad (17)$$

Assuming that all of the reference calibration points are different, it could be assumed, for example, that $REF_{ij}=0$ for (i) not equal to (j) and it could be assumed that $REF_{ij}=REF$ for (i)=(j). For example, this would lead to the assumption that $REF_{12}=0$ and that $REF_{22 \, (etc.)}=C_{REF}$. This produces nine equations and nine unknown calibration factors. These values can be assembled into a [9×9] matrix equation which can be solved using a matrix inverse, as shown below.

$$\{\overrightarrow{FCF}\} = [\Delta T]^{(-1)} \{\overrightarrow{REF}\} \quad (18)$$

where the term $\{\overrightarrow{FCF}\}$ is a [9×1] matrix, where the term $[\Delta T]^{(-1)}$ is a [9×9] matrix, and where the term $\{\overrightarrow{REF}\}$ is a [9×1] matrix.

In more general terms, for N flow paths, the basic equation is:

$$\left\{ \begin{array}{c} \dot{m}_1 \\ \vdots \\ \dot{m}_N \end{array} \right\} \left[ \begin{array}{ccc} FCF_{11} & \cdots & FCF_{1N} \\ \vdots & \ddots & \vdots \\ FCF_{N1} & \cdots & FCF_{NN} \end{array} \right] \left\{ \begin{array}{c} \Delta t_1 - z_1 \\ \vdots \\ \Delta t_N - z_N \end{array} \right\} \quad (19)$$

This requires N calibration points, resulting in $N^2$ equations and $N^2$ unknowns, which can be solved with the matrix inverse:

$$\{\overrightarrow{FCF}\} = [\Delta T]^{(-1)} \{\overrightarrow{REF}\} \quad (20)$$

where the term $\{\overrightarrow{FCF}\}$ is a $[N^2 \times 1]$ matrix,
where the term $[\Delta T]^{(-1)}$ is a $[N^2 \times N^2]$ matrix,
and where the term $\{\overrightarrow{REF}\}$ is a $[N^2 \times 1]$ matrix.

Figure 11:
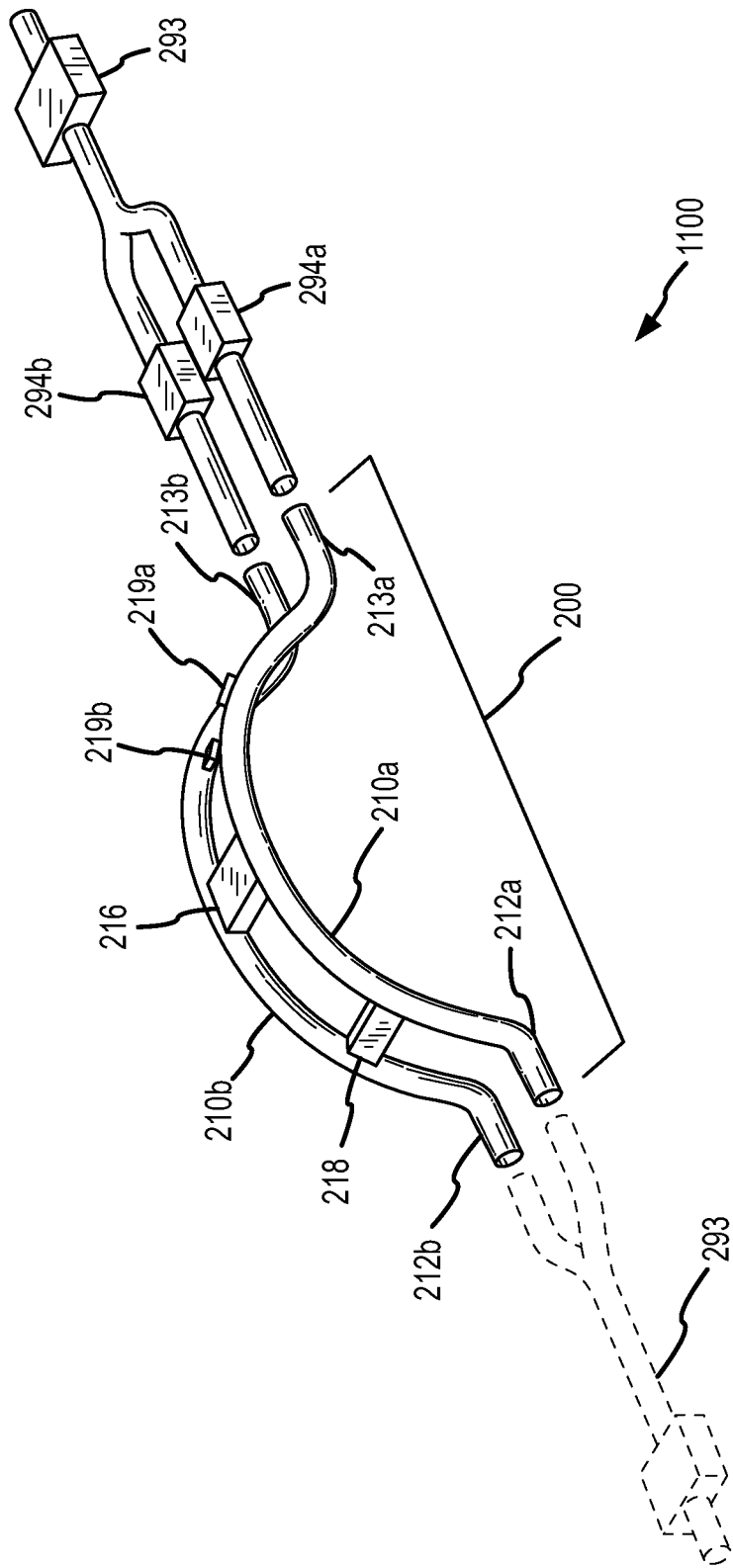
FIG. 11 shows a calibration setup according to an embodiment of the invention.

FIG. 11 shows a calibration setup 1100 according to an embodiment of the invention. The calibration setup 1100 can include first and second valves 294a and 294b and a single reference meter 293. The first and second valves 294a and 294b can be controlled to conduct a first flow stream through the first flow conduit 210a, to conduct a second flow stream through the second flow conduit 210b, or to conduct a combined flow stream through both flow conduits 210a and 210b.

The reference meter 293 is shown located after the three pickoff sensor flow meter 200 and after the valves 294a and 294b. However, as shown by the dashed lines, the reference meter 293 (and/or the valves 294a and 294b) can be located upstream of the flow meter 200.

It should be understood that for calibration setup 1100, the values $REF_1$ and $REF_2$ are generated by the reference meter 293 at different times. For example, during a calibration process, the first flow stream through the first flow conduit 210a is generated by opening the first valve 294a and closing the second valve 294b. The reference measurement subsequently generated by the reference meter 293 is the $REF_1$ value. Then, the first valve 294a is closed and the second valve 294b is opened in order to create the second flow through the second flow conduit 210b. The reference measurement subsequently generated by the reference meter 293 is the $REF_2$ value.

Figure 12:
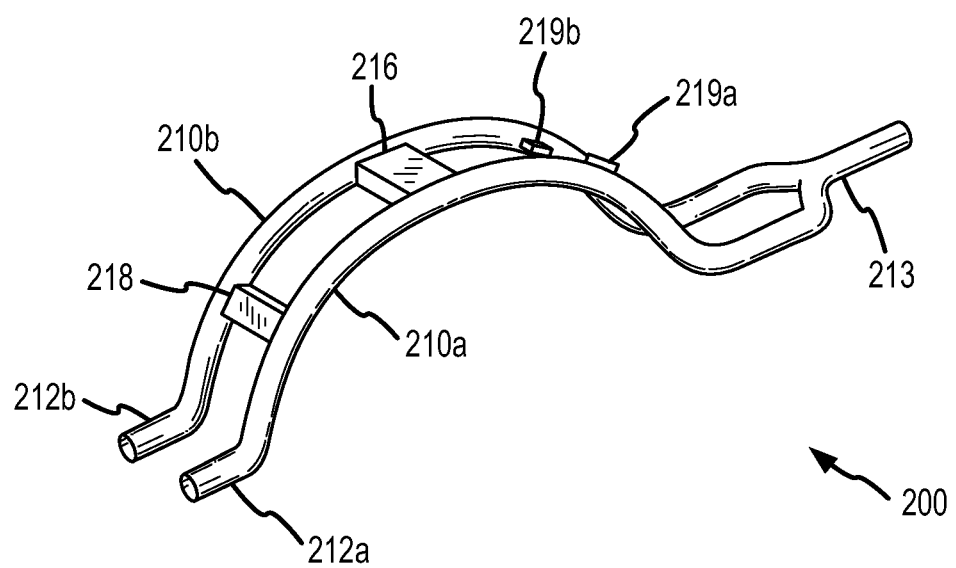
FIG. 12 shows the multiple flow conduit flow meter according to an embodiment of the invention.

FIG. 12 shows the multiple flow conduit flow meter 200 according to an embodiment of the invention. In this embodiment, each flow conduit 210a-210n includes an individual input 212a-212n. However, all of the flow conduits 210a-210n join into a single output 213. Valves can be included upstream of the individual inputs 212a-212n to control the flow through the flow conduits 210a-210n. As a result, the multiple flow conduit flow meter 200 can blend multiple flow streams into a single flow stream at the single output 213. Individual constituents of the output flow stream can be metered by the multiple flow conduit flow meter 200.

In the invention, the flow characteristic measurements are substantially simultaneously obtained for two or more independent flow streams. Unlike the prior art, a driver vibrates two or more flow conduits that are conducting two or more independent flow streams. Unlike the prior art, the flow streams can flow at different flow rates. Unlike the prior art, the flow streams can have different densities. Unlike the prior art, the flow conduits can have differing cross-sectional areas. Unlike the prior art, the flow meter of the invention can include multiple flow conduits. Unlike the prior art, the flow meter can share drivers, eliminating at least one driver.

Advantageously, cost of the flow meter will be lower due to the sharing of components. In addition, the overall size of the flow meter (and a complete metering/dispensing system) can be reduced. In addition, sharing a common driver can reduce power consumption and enables the utilization of a single, smaller electronic power source.

What is claimed is:

1. A calibration method for a multiple flow conduit flow meter, the method comprising:
   zeroing out the multiple flow conduit flow meter;
   zeroing out one or more reference meters in communication with the multiple flow conduit flow meter;
   measuring a first flow through a first flow conduit of the multiple flow conduit flow meter using the multiple flow conduit flow meter and using the one or more reference meters;
   measuring a second flow through at least one additional flow conduit of the multiple flow conduit flow meter using the multiple flow conduit flow meter and using the one or more reference meters; and
   determining two or more flow calibration factors (FCFs) for the multiple flow conduit flow meter using a first flow measurement and an at least one additional flow measurement.

2. The method of 1, with the determining comprising determining the two or more flow calibration factors (FCFs) for the multiple flow conduit flow meter using the $$\text{equation} \left\{ \begin{array}{c} FCF_{11} \\ FCF_{12} \\ FCF_{21} \\ FCF_{22} \end{array} \right\} = \left[ \begin{array}{cccc} \Delta t_1^1 - z_1 & \Delta t_2^1 - z_2 & 0 & 0 \\ 0 & 0 & \Delta t_1^1 - z_1 & \Delta t_2^1 - z_2 \\ \Delta t_1^2 - z_1 & \Delta t_2^2 - z_2 & 0 & 0 \\ 0 & 0 & \Delta t_1^2 - z_1 & \Delta t_2^2 - z_2 \end{array} \right]^{(-1)} \left\{ \begin{array}{c} REF_1 \\ 0 \\ 0 \\ REF_2 \end{array} \right\}.$$

3. The method of 1, with the determining comprising determining the two or more flow calibration factors (FCFs) for the multiple flow conduit flow meter using the $$\text{equation} \left\{ \left\{ \begin{array}{c} \dot{m}_1 \\ \vdots \\ \dot{m}_N \end{array} \right\} \left[ \begin{array}{ccc} FCF_{11} & \cdots & FCF_{1N} \\ \vdots & \ddots & \vdots \\ FCF_{N1} & \cdots & FCF_{NN} \end{array} \right] \left\{ \begin{array}{c} \Delta t_1 - z_1 \\ \vdots \\ \Delta t_N - z_N \end{array} \right\} \right\}$$

$$\left\{ \begin{array}{c} \dot{m}_1 \\ \vdots \\ \dot{m}_N \end{array} \right\} = \left[ \begin{array}{ccc} FCF_{11} & \cdots & FCF_{1N} \\ \vdots & \ddots & \vdots \\ FCF_{N1} & \cdots & FCF_{NN} \end{array} \right] \left\{ \begin{array}{c} \Delta t_1 - z_1 \\ \vdots \\ \Delta t_N - z_N \end{array} \right\}.$$

* * * * *

UNITED STATES PATENT AND TRADEMARK OFFICE
CERTIFICATE OF CORRECTION

PATENT NO.     : 9,719,838 B2                          Page 1 of 1
APPLICATION NO. : 14/547746
DATED          : August 1, 2017
INVENTOR(S)    : Charles Paul Stack et al.

It is certified that error appears in the above-identified patent and that said Letters Patent is hereby corrected as shown below:

On the Title Page

(72) Inventors: replace "Charles Paul Stack, Las Vegas, CO" with -- Charles Paul Stack, Las Vegas, NV --

In the Specification

Column 12, Equations 5 and 6, that portion of the equations reading $(1-M_1 \times Tm_1)$ should read -- $(1-Tc_1 \times Tm_1)$ --

Column 15, Line 46 replace "$FCF_{1i}$" with -- $FCF_{11}$ --

Signed and Sealed this
Twenty-ninth Day of May, 2018

Andrei Iancu
*Director of the United States Patent and Trademark Office*